(12) United States Patent  
Brunel (10) Patent No.: US 8,520,206 B2  
(45) Date of Patent: Aug. 27, 2013

(54) METHOD FOR THE RHEOLOGICAL CHARACTERISATION OF A COMPLEX MEDIUM

(75) Inventor: Laurent Brunel, Peyrins (FR)

(73) Assignee: Formulaction, L'Union (FR)

( * ) Notice: Subject to any disclaimer, the term of this patent is extended or adjusted under 35 U.S.C. 154(b) by 2 days.

(21) Appl. No.: 13/320,598

(22) PCT Filed: May 12, 2010

(86) PCT No.: PCT/EP2010/056516
§ 371 (c)(1),
(2), (4) Date: Nov. 15, 2011

(87) PCT Pub. No.: WO2010/130766
PCT Pub. Date: Nov. 18, 2010

(65) Prior Publication Data
US 2012/0062891 A1    Mar. 15, 2012

(30) Foreign Application Priority Data
May 15, 2009    (FR) ..................... 09 02362

(51) Int. Cl.
*G01N 21/00*    (2006.01)
(52) U.S. Cl.
USPC ........................................ 356/338
(58) Field of Classification Search
USPC ........................................ 356/338
See application file for complete search history.

(56) References Cited

U.S. PATENT DOCUMENTS

| | | | | |
|---|---|---|---|---|
| 6,002,480 | A * | 12/1999 | Izatt et al. ..................... | 356/479 |
| 7,312,868 | B2 | 12/2007 | Brunel | |
| 7,777,891 | B2 * | 8/2010 | Hasegawa ..................... | 356/485 |
| 7,782,458 | B2 | 8/2010 | Snabre et al. | |

FOREIGN PATENT DOCUMENTS

| | | |
|---|---|---|
| EP | 1 720 000 | 8/2008 |
| FR | 2 841 983 | 1/2004 |
| FR | 2 860 300 | 4/2005 |
| WO | 2005/031324 | 4/2005 |

OTHER PUBLICATIONS

International Search Report dated Aug. 17, 2010, corresponding to PCT/EP2010/056516.
Zakharov, et al. "Multispeckle Diffusing-Wave Spectroscopy With A Single-Mode Detection Scheme"; American Physical Society, College Park, MD. vol. 73, No. 1; Jan. 1, 2006; pp. 11413/1-011413/5.

* cited by examiner

*Primary Examiner* — Tu Nguyen
(74) *Attorney, Agent, or Firm* — Young & Thompson (57) ABSTRACT

A method for quantitatively determining the viscoelastic properties of a complex medium with suspended particles in suspension, which involves: characterizing the medium opacity by measuring the medium's transport length l*; introducing a sample of the medium into a flask; placing the flask in a thermostatically-controlled measuring chamber; projecting a coherent light beam on the sample and detecting scattered light as a series of sequenced images; analyzing the movement of particles based on time by calculating the inter-image distance $d_2$ and the ratio $d_2/d_{2max}$; and establishing an analytical expression E putting into direct relationship, the measured l*, the ratio $d_2/d_{2max}$ and the mean square displacement MSD for the purpose of calculating the medium's viscous and elastic moduli.

17 Claims, 5 Drawing Sheets fig. 1

METHOD FOR THE RHEOLOGICAL CHARACTERISATION OF A COMPLEX MEDIUM

FIELD OF THE INVENTION

This invention relates to the field of physical characterization of complex media, and more particularly the measurement of rheological properties of industrial compositions, in particular opaque products.

BACKGROUND OF THE INVENTION

It has as its object a method for quantitative determination of viscoelastic properties of a complex and generally opaque medium, based on the calculation of the movement of particles in suspension starting from the detection of the light scattered by the medium. A device that is designed for the implementation of this method is also the object of the invention.

It is very useful for manufacturers to characterize—from the standpoint of their rheological properties—the products that they are developing and whose quality they are monitoring, for example for following the evolution over time of the viscosity of a formulation or for comparing the viscoelastic properties of two products of close formulations. To do this, viscometers and rheometers with rotating and oscillating moving bodies that measure the resistance to shear and to flow are widely used and make it possible to calculate the corresponding viscosity. The principle is based on the measurement of the force that is necessary to the rotating or oscillating of a gauge that is in contact with the product, with the gauge that can be a rod immersed in the product, or else flat or conical plates between which a film of the product to be tested has been spread.

In all of the cases, a sample is placed in contact with the gauge that is to be cleaned between each measurement, which represents a significant loss of time and introduces risks of misaligning or even degrading the device, and finally a lack of reliability of the measurements. The tested sample can only be used once. However, when the evolution of a composition over time is studied, or when it is desired to compare several formulas with one another, it is preferable to preserve the same sample for making (or redoing) all of the necessary measurements, so as to reduce as much as possible the possible variations of the composition of the products that are prepared and those that are inherent to human manipulations. Incidentally, these devices can be used only by individuals who have a high level of expertise, knowing to calibrate them and to implement them correctly to obtain reliable results. Routine use under production conditions is therefore virtually impossible.

To prevent these problems, a method that is based on optical measurements has been sought. It is actually known to determine certain properties that depend on the rheology of a complex medium by the measurement of the kinetics for movement of particles of a known size in suspension in a medium. The Brownian motion of these particles corresponds to trajectories whose characteristics are strongly tied to rheological properties and is analyzed by an elastic component (preservative part) and a viscous component (dissipative part).

The prior art teaches the possibility of following the trajectory of Brownian particles by detecting the time change of the speckle field produced by a laser wave that diffuses into the medium under study, using an optical technique that has been known for about 30 years under the name of DWS (Diffusing Wave Spectroscopy). The speckle grains are light interferences produced by the superposition of light rays that have travelled different paths in the medium. The method is based on the detection of the intensity variation of the light received by a single detector or by the pixels of a video camera (by scattering or by back-scattering according to the selected technique). The dynamics of the speckle field makes it possible to draw conclusions about the dynamics of the particles that have contributed to the scattering of the light.

If the number of time measurements of the light intensity is adequate, it is possible to derive a time auto-correlation function ($g_2$). The use of a video camera as a detector offers the possibility of acquiring many more signals during the same time period and therefore makes it possible to obtain an auto-correlation of good quality in much less time by exploiting the ergodicity property that establishes that it is equivalent to averaging signals in various positions in space and averaging signals that are acquired in successive series over time. The prior art also described an alternative solution that is based on the use as a detector of a double cell (EP1720000).

In the case where a camera is used, the applicant advantageously introduced a more practical method for calculating the decorrelation of the speckle, by quantification of the inter-image distance, denoted $d_2$ (as presented in detail in WO 2005/031324). The inter-image distance represents the movement of the particles over the time period that separates two images. This method makes it possible to access the movement dynamics of particles, a value that gives information in particular on the drying rate (or the loss of fluidity) of a mixture.

It does not make it possible, however, to attain the different components that account for rheological properties, namely the elastic module $G'(\omega)$ and the viscous module $G''(\omega)$ of the medium, whereby this distinction is often valuable and even essential for characterizing and predicting the behavior of a mixture.

Prior studies in this field have described the principle of the determination of the viscous and elastic moduli in two stages. The first stage makes it possible to pass from the optical signal to the movement of particles over time (kinetics of movement of the particles, formalized by the Déplacement Quadratique Moyen (DQM or MSD for Mean Square Displacement in English), by means of a suitable mathematical modeling and a certain number of approximations (Weitz—1993). The second stage (Mason—1995) is based on the Stokes-Einstein Law that is generalized for deducing from this kinetics the viscous and elastic properties of the sample, i.e., the value of $G'(\omega)$ or $G''(\omega)$.

However, the fluids targeted here are complex fluids and are thus characterized by the numerous parameters that are involved in taking their properties into account, unlike simple fluids whose behavior can be easily modeled. In particular, the models that are established for connecting optical measurements to physical properties of the media being studied involve the statistical distribution P(s) of the lengths of paths of photons between the light source and the receiver (between the laser and the camera). However, the direct calculation of the function P(s) in practice is possible only for simple cases, using semi-completed flasks or blades. Digital simulations could be applied for calculating the function P(s) of the complex fluids, but this type of solution can no longer be considered within an industrial context, because it is impossible to control all of the optical parameters and the laws that describe them. The calculation periods are inconsistent for offering a quick measurement result to the user, and their final precision is far from being ensured. These simulations have shown in particular that the greatest source of inaccuracy was the lack of knowledge of the parameters that influence the first of the two stages, i.e., the relationship existing between the inter-image distance $d_2$ and the actual movement of the MSD particles.

SUMMARY OF THE INVENTION

The thus posed problem, the object of this invention, is then summarized to propose a simple and direct manner of obtaining MSD from $d_2$ for complex and opaque fluids by means that can be implemented under industrial conditions, with a reliable and precise result. To do this, the inventors have defined an operating protocol, by which a sample of a complex medium is subjected to an optical measurement that provides an analysis of the movement of the particles by a known method, with this measurement being implemented under strictly defined conditions and its results being analyzed using a predefined model that can be modulated by calibration based on a variable parameter of the medium.

An optical measurement of the movement can be implemented, for example, by projecting a laser beam on a sample and by recording the electromagnetic field that is produced by the light that is scattered by said sample in the form of matrix images. A direct analysis of the speckle dynamics produced by the scattering of the laser beam passing through the analyzed medium can be obtained, for example, according to the method that is described in WO 2005/031324. There is thus access to the values of the inter-image distance $d_2$, from which the curve of variation $d_2/d_{2max}$ can be deduced based on time, with $d_{2max}$ being the asymptotic value that $d_2$ assumes after a certain time. It should be noted that at this stage, it is possible, for example, to study the drying rate of a liquid film, but not to obtain rheological information on the product during its drying. This invention has as its object to provide this type of information, thus meeting a need of the laboratories wanting to follow the rheology during the formation of a film. It should also be noted that in accordance with the specifications of the invention, the analyses are made on three-dimensional samples and not on films spread manually. Such an instrument can thus take this measurement in situ.

It appeared that, to be exploitable in an efficient model, the measurement of $d_2$ is to be implemented under strictly defined conditions. It was established by the applicant that the essential and adequate parameters to take into account during the measurement were the size of the sample (and therefore the shape of the receptacle), the strict immobility of the device and the stability of the temperature of the sample, but also that of the measuring device. Actually, the viscoelastic parameters of the products change based on the temperature. Because of the extreme sensitivity of the measurement, for the implementation of the invention, it has proven essential to ensure thermal regulation of the measuring device and also to prevent hot air movements from developing by convection between the sample and the camera. In addition, all of the vibrations in the environment can be transmitted to the analyzed sample and generate a stronger parasitic signal than the valid signal.

As explained above, the result of the optical measurement and its analysis in terms of the displacement rate $d_2(t)$ is to be connected to the mean square displacement MSD. According to the invention, this operation is implemented using a predefined model that can be modulated based on a variable parameter of the medium.

The expression of the model that is proposed here makes it possible to adapt it to a variable of the medium. The optical properties, in particular the opacity of the product, are, of course, variable from one product to the next. It was shown that the transport length l* is the primary parameter that accounts for the optical properties of the product that influences the lengths of the trajectories of photons. It was also shown that the physical parameters that can have an influence (diameter of the particles, refraction index of the materials that constitute the different product phases, forms of particles) have less importance in obtaining the result, with their impact being for the most part already taken into account in the parameter l*. This is why, according to the model that is proposed here, l* is the only variable parameter that influences the curve $MSD(d_2/d_{2max})$, which is particularly advantageous to the extent that l* can be measured directly by optical techniques that are known to one skilled in the art.

The invention thus has as its object a method for determination of the viscoelastic properties of a complex medium starting from the movement of particles in suspension, in which a sample of the medium is placed in a device for measuring the light that is scattered by the particles in suspension, able to project a coherent light on said sample, and to detect and analyze the scattered light for calculating the inter-image distance $d_2$, whereby said method comprises the stages that essentially consist in:

a) Characterizing the opacity of the medium by measuring the transport length l* of said medium, b) Introducing a sample of said medium into a flask of given dimensions, c) Placing the flask in a thermostatically-controlled measuring chamber of said device for measuring the movement of the particles, d) Projecting a coherent light beam on the sample and detecting the light that is scattered by the particles in the form of a series of sequenced images, e) Analyzing the movement of the particles based on time by calculating the inter-image distance $d_2$ and the ratio $d_2/d_{2max}$, f) Establishing an analytical expression E putting into direct relationship, for the value of l* that is determined in stage a), the ratio $d_2/d_{2max}$ and the mean square displacement MSD for the purpose of calculating the viscous and elastic moduli of the medium.

It is known to determine the transport length l* of a concentrated and/or opaque medium at different time intervals. This value is representative of the penetration of the light into the medium and makes it possible to quantify its opacity. The determination of l* can be done, for example, according to the method that is the object of the patent FR 2 841 983.

A device for measuring the light that is scattered by the particles in suspension may be similar to that described in WO2005/031324, at least relative to the optical module and the means for analyzing and calculating the signal, i.e., the elements that are able to project a coherent light on said sample and to detect and analyze the scattered light for calculating the inter-image distance $d_2$ and the ratio $d_2/d_{2max}$. This technique is based on the detection of the light by back-scattering, with analysis of the decorrelation of the speckle field by means of the inter-image distance $d_2$.

The expression of the model that is proposed here advantageously contains at least one adjustable coefficient and preferably three coefficients, which make it possible to adapt the model based on a variable parameter of the medium, in this case with l*. This is also the reason for which, advantageously, the adjustable coefficients that are selected are representative of the different values that l* can assume in the different media to be analyzed. Thus, according to an advantageous characteristic of the invention, in stage f), the expression E is expressed using at least one, and preferably three, variable coefficients that can be expressed based on the opacity of the medium, and said expression E is adjusted based on the value of l* that is determined in stage a), before the calculation of the viscous and elastic modules of the medium.

One original feature of the invention is that these coefficients are determined for each medium by a particularly efficient calibration method. Thus, according to a preferred characteristic of the invention, in stage f), the variable coefficients that are used for establishing the expression E are functions of l*, selected and recorded in a database that was previously constituted according to the stages that consist in:

i) Preparing—in flasks of given dimensions, a range of samples of a simple fluid of known viscosity with different opacities, ii) For each sample of the range, Determining the value of l*, Calculating the theoretical curve $MSD_T(t)$ based on time using the Stokes-Einstein Law, Analyzing the movement of the particles based on time for calculating the inter-image distance $d_2$ and the ratio $d_2/d_{2max}$ and for plotting the experimental curve $MSD_E(t)$ using the expression E, Seeking the values of said coefficients for obtaining a theoretical curve $MSD_T(t)$ that coincides with said experimental curve $MSD_E(t)$, iii) For each coefficient, tracing the calibration curve representing the evolution of its value based on l*, and iv) Recording each of said curves in a database that can be called up in stage f).

This method therefore consists in expressing the coefficients based on the opacity that is expressed by the value of l* measured for fluids of constant viscosity at a given temperature (simple fluids). When a complex sample is analyzed, its opacity is measured in advance, and values of the calibration coefficients obtained for the value of l* of the simple fluid of the same opacity are introduced into the model. It thus is possible to implement, in a particularly advantageous manner, an independent calibration of the temperature and other measuring conditions.

Thus, an essential characteristic of the proposed model is the fact that once the relationship between $d_2/d_{2max}$ and MSD is established for the particular case of simple fluids, this relationship can be used for all of the complex fluids. In a corollary manner, the proposed method makes it possible to plot the curve $MSD(d_2/d_{2max})$ starting from knowing only l*. One of the essential advantages that derive therefrom is that the geometry of the sample is not imposed and that it is possible to use realistic (three-dimensional) flasks that are suitable for tests of a large variety of products under industrial conditions, with neither manipulation nor destruction of the sample.

In addition, to improve the quality and the effectiveness of the modeling proposed by the applicant, the latter can preferably meet the following requirements:

It is based on analytical expressions that are selected after observation of the experimental measures for best adapting to the latter;

The analytical expressions are simple for reasons of calculating performance (the final software of the instrument will have to calculate the thousands of MSD in several seconds);

It contains a minimum of free parameters for purposes of simplicity and robustness.

As much as possible, these parameters should have a physical meaning to help interpret possible measurement flaws.

Thus, according to a particular embodiment of the method according to the invention, in stage f), the analytical expression adopts the following form:

$$(d_2/d_{2max})^2 = 1 - \exp\{-4(A_2 DQM\, k_o^2/6)^{[B+C\,log_{10}(A\,DQM\,k_o^2/6)]}\}$$

in which A, B, and C are three variable coefficients, and $k_o$ is the wave number, depending on the wavelength of the projected light.

According to a particularly advantageous embodiment of the method according to the invention, said variable coefficients A, B, and C are selected in such a way that the calibration functions A(l*), B(l*), and C(l*) are able to be represented by straight lines, which can be made by carefully selecting a logarithmic or linear scale for the axes of the abscissas or ordinates.

According to a preferred characteristic of the invention, in stage d), the detection of said series of images is carried out according to an increasing pace, in one or more bursts. Actually, so as to explore a large time scale range (from $10^{-4}$ s to $10^{+5}$ s) while avoiding having to acquire and to manage an excessive mass of information, it is preferable to distribute the picture-taking over a logarithmic time scale. Image acquisition therefore is not done with a constant pacing between each image, as is the case with a conventional video film. It is possible to use an electronic clock that controls the acquisition of images in a single film in which views are taken at increasingly long intervals. Alternately, it is possible to produce several small video films, each burst comprising up to 1,000 images, for example, taken at a constant image pace, but according to a different pace for each burst.

In a preferred embodiment, during stage d), the detection of said series of images is carried out in a single burst at a pace that increases according to a geometric progression over at least two decades, with four to five decades being more preferred. This is of considerable advantage for covering the entire range of values of $d_2$ that are necessary for determining the two terms G'(ω) and G"(ω).

In certain applications, it is advantageous to determine the rheological properties of a sample that is subjected to temperatures that are far from ambient temperature. However, the elements that form the optical module, namely essentially the coherent light source and the detector of the scattered light, are sensitive to the variations of temperatures, and it is preferable that they operate in an interval that is generally between 5° C. and 50° C. This is why an embodiment of the inventive method is proposed here, according to which method the optical functions are carried out from the exterior of the measuring chamber: to do this, the elements that form the optical module, namely essentially the coherent light source and the detector of the scattered light, are mounted outside of the measuring chamber and point to the sample through one of its walls in which the holes were provided. The temperature of the measuring chamber can then be selected at levels that are lower than 5° C. and higher than 50° C. Thus, in stage d), the light can be projected and detected using an optical module that is placed on the exterior of the measuring chamber, the latter having a wall that is penetrated by windows.

According to a preferred embodiment of the method according to the invention, in stage c), a number of sample flasks are placed in several contiguous housings located in the measuring chamber. This approach makes it possible to ensure stabilization of the measuring conditions (temperature in particular) for several flasks at the same time, which, of course, optimizes the operation of the device. If the optical module is mounted on the exterior of the measuring chamber, the wall of the latter is provided with as many windows as housings to allow the passage of projected and scattered light.

In this embodiment of the method that is the object of the invention, in an advantageous manner, the optical module is placed successively facing each of said flasks, and stages d) to f) are repeated for calculating the viscous and elastic moduli of each of the sampled media. The measuring chamber thus remains stationary, which prevents creating air movements in the chamber and shocks that would be detrimental to the precision of the measurement.

Furthermore, for the reasons specified above, the conditions for carrying out measurements are strictly monitored. Thus, according to one characteristic of the invention, stage d) is carried out under conditions of stability and thermal uniformity of the samples and the measuring chamber in the absence of air convection movements between the optical module and the sample, and vibrations obtained from the surrounding environment. In particular, it is appropriate to stabilize the temperature of the atmosphere of the measuring chamber because non-homogeneous temperatures entrain movements by convection, which have an impact on the quality of the optical measurement. The embodiments described above are combined to produce these conditions. Other means also contribute thereto and are incorporated in the device for determination that will be described in detail later.

Thus, by initiating certain simplifications that are carefully selected within the number of variable parameters to be taken into account and by defining a method for calculating results based on a great precision of optical measurements made under monitored conditions, combined with a calibration mode that makes possible the rapid calculation for any type of medium, this invention offers a simple and quick access to the quantification of viscoelastic properties of complex media, including opaque complex media, with neither manipulation nor destruction of the sample. The method can then be applied to tracking the evolution of the same sample over time or the quantitative comparison of two products of close formulation.

A device that meets the above-mentioned requirements and that makes possible the implementation of the method described above is also the object of this invention. More specifically, a device for determining viscoelastic properties of a complex medium starting from the movement of particles in suspension is claimed, comprising means for projecting a coherent light on said medium and means for detecting and analyzing the scattered light for calculating the inter-image distance $d_2$, whereby said device comprises:

An optical module that comprises, on the one hand, a coherent light source that is able to project a beam to a sample of the medium that is to be analyzed, and, on the other hand, means for detection of the scattered light by said medium, in the form of successive matrix images, whereby said means are combined with a unit for image analysis that is able to provide values of the inter-image distance of the sample, A thermostatically-controlled measuring chamber that is equipped with at least one housing that is able to accommodate a flask of given dimensions that contains a sample of said medium, at a suitable distance from the optical module, Means for recording and processing data, comprising means for acquisition of values of $l^*$ that characterize the opacity of the media to be analyzed, means for analysis and calculation that are able to put into direct relationship, for a value of $l^*$, the ratio $d_2/d_{2max}$ and the mean square displacement MSD, for the purpose of calculating the viscous and elastic moduli of the medium.

The measuring chamber is thus a chamber that defines a closed space. The housing that supports the sample is designed so that the flask that is used is locked in a specified position that is adequate relative to the optical devices. It is thus possible both to immobilize the atmosphere through which light rays pass and to keep the sample at a fixed temperature. These arrangements contribute in a critical manner to the good operation of the device and to obtaining directly exploitable quantitative results.

According to a particular embodiment of the device that is the object of this invention, said at least one housing that accommodates a flask is located in a thermostatically-controlled heating block, itself placed in the interior of the measuring chamber, at a suitable distance from the optical module.

In an advantageous variant of the device that is the object of the invention, the optical module is placed on the exterior of the measuring chamber, the latter having an insulating wall that is penetrated by windows for the passage of projected and scattered light. It thus is possible to study media at extreme temperatures (i.e., lower than 5° C. and higher than 50° C.) depending on what the user wants, without the elements of the optical module suffering too high or too low a temperature.

According to another characteristic of the device, which is the object of the invention, the coherent light source that is projected on the sample is a laser source, and the means for detecting the scattered light comprise a matrix sensor of the video camera type.

In addition, the device according to the invention preferably also comprises means for neutralizing vibrations from the surrounding environment, comprising feet made of damping material and a non-vibrating support structure, selected from among: a honeycomb table, an air cushion table, a weighted straw mattress. The feet are selected for their characteristics relative to mechanical resonance frequencies of the device.

BRIEF DESCRIPTION OF THE DRAWINGS

Other advantages and characteristics of the invention will emerge from reading the description below of an embodiment that is provided by way of non-limiting example, illustrated by the attached drawings, in which.

DETAILED DESCRIPTION OF THE INVENTION

Example 1

Device for Determining Viscoelastic Properties

Figure 1:
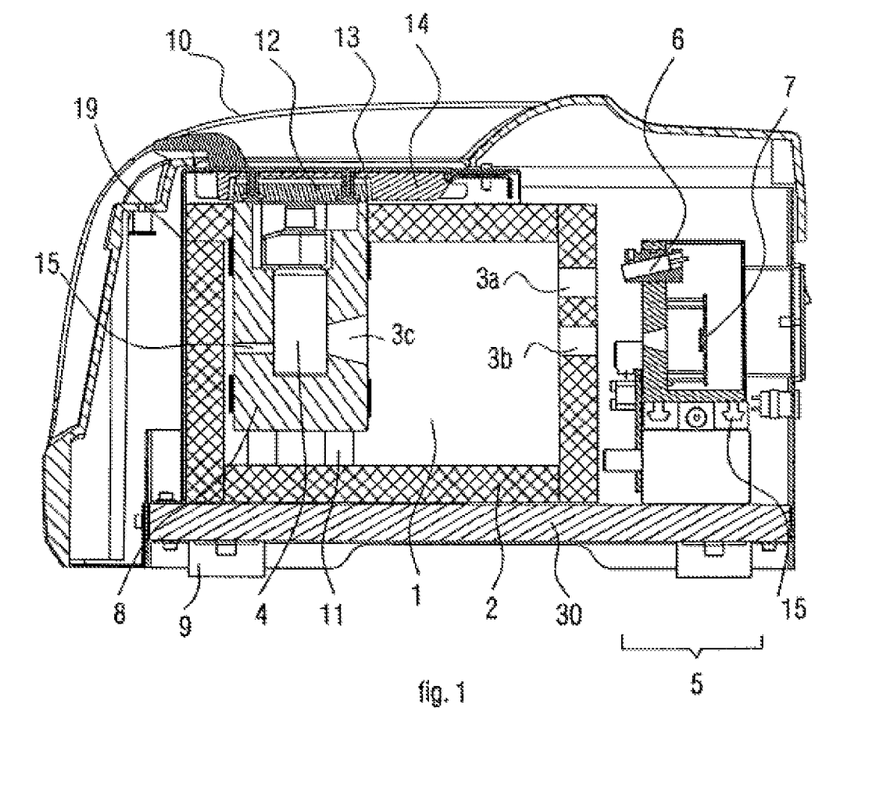
FIG. 1 is an exploded perspective view of a device according to the invention.
Figure 2:
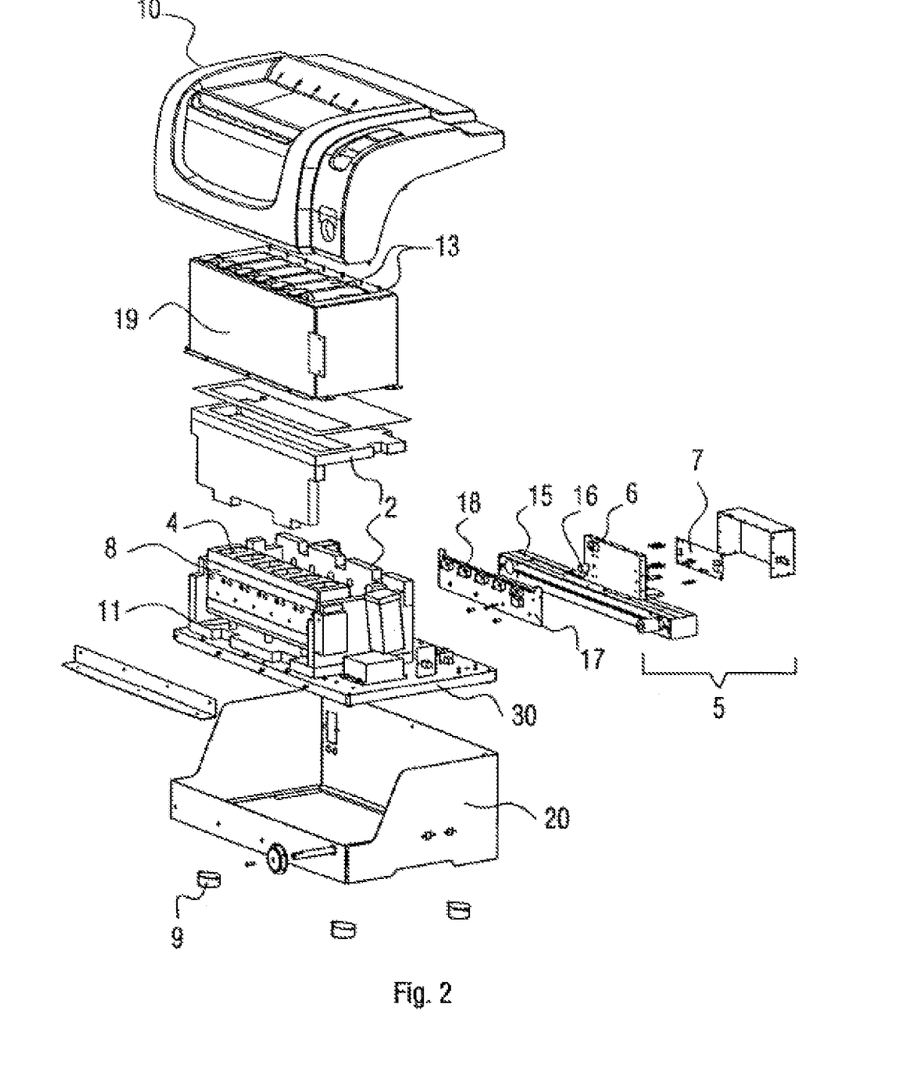
FIG. 2 is a cutaway view of the same device.

The device for determining viscoelastic properties of a complex medium illustrated in FIGS. 1 and 2 comprises the measuring chamber 1 and the optical module 5, protected by the upper cowl 10 and the lateral cowl 20, resting on the plate 30 that is equipped with damping feet 9. The measuring chamber 1 is delimited by the insulating wall 2, penetrated by windows 3a and 3b. The optical module 5, arranged on the exterior of the chamber 1, comprises the laser source 6 that is placed perpendicular to the window 3a and a video camera 7 that is placed perpendicular to the window 3b. It comprises a mother card that is able to analyze the movement of the particles based on time, and it is connected to data-processing and computing means that make it possible to put the ratio $d_2/d_{2max}$ and the mean square displacement MSD into direct relationship for the purpose of calculating the viscous and elastic moduli of the medium.

The housing 4 that can accommodate a flask is surrounded by the heating block 8, resting on the lower wall of the measuring chamber 1 by means of the feet 11. The heating block 8 is penetrated at 3c for the passage of the incident and back-scattered light. It is closed by the heating plug 12, accessible by the flap 13, itself equipped with the insulation 14. The heating block 8 is combined with means for monitoring and regulating temperature (not shown). The cylindrical flask with an exterior diameter of 27.5 mm is held in place by the pusher 15.

As shown in FIG. 2, the heating block 8 comprises six housings 4 that are accessible by six flaps 13 that are mounted on the support 19. The optical module 5 is mounted to slide on the rail 15 that is equipped with the stop 16. The position cam 17 that is equipped with mechanical sensors 18 works with the rail 15 to place the optical module 5 at the windows 3a, 3b.

Example 2

Principle of the Determination of Viscoelastic Properties

Figure 5:
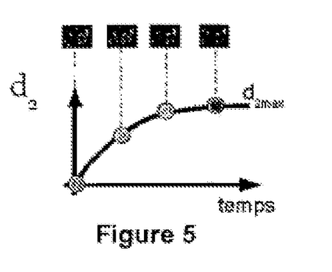
FIG. 5 is a curve of the inter-image distance, denoted $d_2$, as a function of time, toward a maximum value denoted $d_{2max}$.

The camera collects the interference figure created by the laser that has scattered into the product for acquiring a series of images. The first is taken as a reference. Next, for each subsequent image, the inter-image distance, denoted $d_2$, is calculated between the latter and the reference image. At $t_o$, $d_2$ is zero, and then over time, its value converges asymptotically toward a maximum value denoted $d_{2max}$.

The graph presented in FIG. 5 illustrates this evolution.

Figure 6:
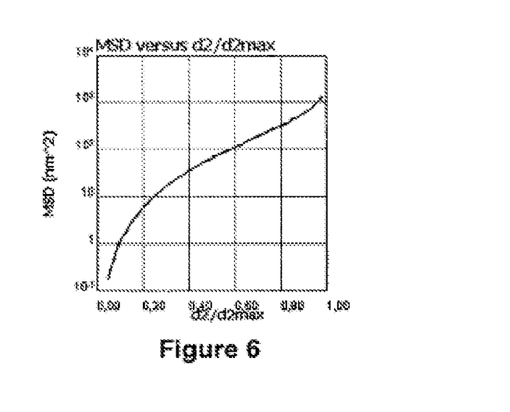
FIG. 6 is a curve constructed from the calculated mean square displacement (MSD) as a function of time and the corresponding $d_2/d_{2max}$ for a corresponding time from the curve of FIG. 5.

It is now advisable to determine the mean square displacement MSD by constructing the curve $MSD(d_2/d_{2max})$ starting from knowing only l*. For reasons of efficiency of the conversion of $d_2$ into MSD, an empirical model was created for providing an analytical expression of the curve $MSD(d_2/d_{2max})$.

The MSD is homogeneous to the square of a length.

This relation $MSD(d_2/d_{2max})$ has the form as depicted in FIG. 6, where the y axis is on the logarithmic scale:

The approach that is adopted is as follows:

We measured the curve $d_2(t)$ of particles of known diameter in suspension in a simple fluid that is known and therefore characterized by its viscosity.

MSD(t) can be easily calculated with the Stokes-Einstein relation.

$$MSD = 6Dt \quad (Eq\ 7)$$

with D: diffusion coefficient of the particles.

By eliminating the time variable, it is possible to connect $d_2$ and MSD for a given l*. The value of l* is set by the concentration of particles of the model product. If this concentration is low (<1%), it has virtually no influence on the viscosity of the mixture: the viscosity of the mixture remains that of the simple fluid.

For example, for particles of titanium dioxide ($TiO_2$) with a 1 μm diameter in suspension in a glycerol/water mixture, the viscosity is constant and can be measured with precision. Concentrations by volume of particles of 1%, 0.5%, 0.2%, 0.1%, 0.05% and 0.01% provide different opacity levels respectively with values of l* of 80, 160, 390, 750, 1,600 and 7,600 μm for the wavelength that is used.

For the sake of efficiency of the conversion of $d_2$ into MSD explained above, an empirical model is proposed that provides an analytical expression of the curve $MSD(d_2/d_{2max})$ developed from the correlation function $g_1$.

The traditionally used correlation functions are $g_1(T)$ and $g_2(T)$ with:

$g_1(T)$ is the correlation function of the electrical field $g_2(T)$ is the correlation function of the intensity of the electrical field that is effectively measured by the sensor.

$$g_1(T) = <E(t)E(t+T)>/<E^2> \quad (Eq\ 3)$$

$$g_2(T) = <I(t)I(t+T)>/<I^2> \quad (Eq\ 4)$$

$g_1$ and $g_2$ are connected by the formula (Siegert relation)

$$g_2(T) - 1 = \beta |g_1|^2 \quad (Eq\ 5)$$

in which β is a number from 0 to 1 that takes into account the size of the sensor. For small camera pixels having the size of the speckle grain, β=1.

There is a simple relation between $d_2$ and $g_2$:

$$g_2 - 1 = 1 - (d_2/d_{2max})^2 \quad (Eq\ 6)$$

The analytical expressions supplied by the literature provide $g_1(T/TCD)$ for the case of Brownian particles in a simple fluid as is the case for the suspensions of selected calibration. The time y is standardized by the characteristic diffusion time CDT, which depends only on the diffusion coefficient D used in the Stokes-Einstein relation (Eq 7). This makes it possible to have a common function for all of the movements of particles in all of the simple fluids.

It is then possible to connect $d_2/d_{2max}$ to $g_1$ with the equations 5 and 6 (for us, β=1):

$$(d_2/d_{2max})^2 = 1 - g_1^2 \quad (Eq\ 9)$$

Thus, for the simple fluid, on the one hand, MSD is known for the given T/TCD (Stokes-Einstein Law), and therefore $d_2/d_{2max}$ is known for this T/TCD, and finally, it is possible to connect MSD to $d_2/d_{2max}$.

It is possible to rewrite the Stokes-Einstein relation (Eq 7) based on T/TCD:

$$DQM = 6DT = 6/k_0 T/TCD \quad (Eq\ 8)$$

with $TCD = 1/(k_o D)$: Characteristic diffusion time.

$K_o$: wave number=constant since the wavelength of the laser is set.

D: diffusion coefficient of the particle.

Here is an example of a proposed formula with three parameters (A, B, C):

$$g_1(T/TCD) = \exp\{-2(A\ T/TCD)^{\wedge}[B + C\ \log_{10}(A\ T/TCD)]\}$$

Finally, it is possible to formulate directly the relationship between MSD and $d_2/d_{2max}$ $$(d_2/d_{2max})^2 = 1 - \exp\{-4(A\ DQM\ k_0^2/6)^{\wedge}[B + C\ \log_{10}(A\ DQM\ k_0^2/6)]\}$$

This relationship that is established between $d_2/d_{2max}$ and MSD for the particular case of simple fluids can now be used for all of the complex fluids, provided that the applicable values of A, B, and C are defined.

Example 3

Calibration

It therefore remains to trace—experimentally—the curves A(l*) B(l*) C(l*) for several l*. For each l*, A, B, and C are adjusted by numerical means or by observing the graph providing MSD(t) with its two axes on a logarithmic scale. The height of the straight line is given by the viscosity of the model fluid, the size of the model particles, and the temperature (Stokes-Einstein Law).

It is possible to do the same thing for all of the l* of the range of l* corresponding to the fields of application of the instrument. We found by experiment that the curves A(l*) B(l*) C(l*) are quite uniform, and it is therefore sufficient to measure A, B, and C for 4 or 5 values of l* and next to interpolate to obtain our 3 curves.

A makes it possible to adjust to the viscosity of the fluid.

B makes it possible to comply with the diffusion law provided by Stokes-Einstein (slope=1 of MSD(t) of log/log).

C makes it possible to preserve this slope 1 with all time scales (linearization).

A calibration result is provided, for example, by the simple expressions of A, B, and C.

Figure 7:
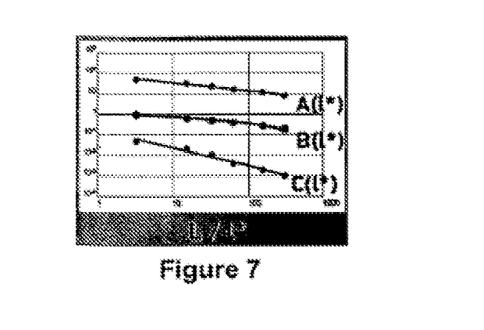
FIG. 7 shows the calibration curves for $A(l^*)$ $B(l^*)$ $C(l^*)$.

Cell size=$L$=25 mm $A(l^*)=10^{\wedge}(-0.4\times\log_{10}(L/l^*)+1.95)$ $B(l^*)=-0.41\times\log_{10}(L/l^*)+1.18$ $C(l^*)=10^{\wedge}(-0.79\times\log_{10}(L/l^*)-0.46)-0.119$ The corresponding curves are shown in FIG. 7.

Figure 3:
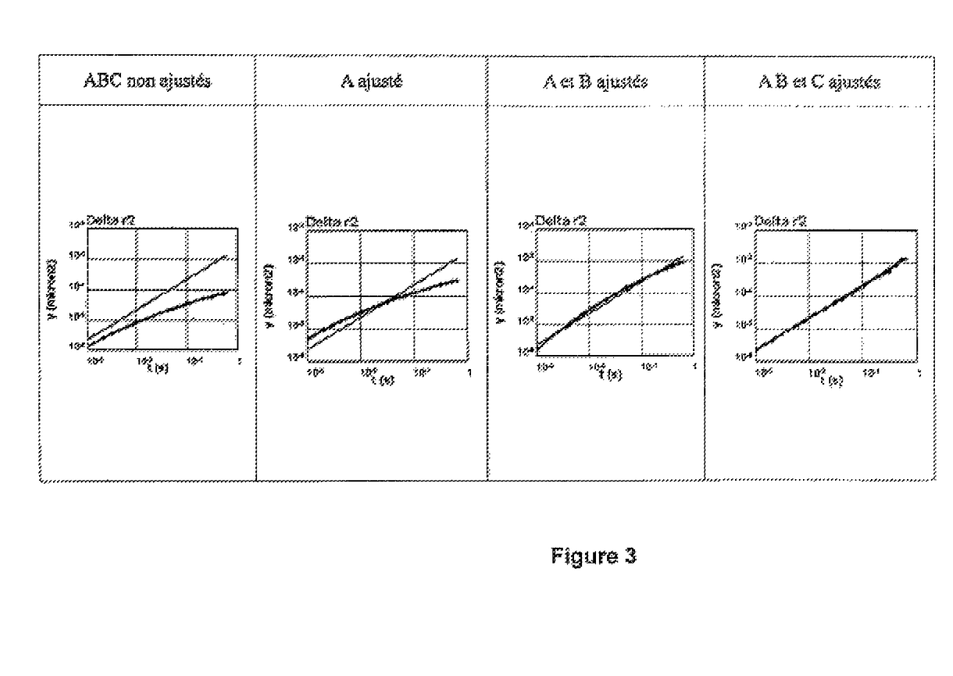
FIG. 3 shows the adjustment of the variable coefficients.

Here is an example of this calibration for the case of $TiO_2$ particles in suspension in glycerol (1% by volume). FIG. 3 shows how the parameters A, B, C make it possible to perfectly adjust the curve experimentally to the theoretical curve.

Example 4

Determination of the Viscoelastic Properties of a Product

Two dessert creams of different brands and formulations (F1 and F2) but claiming the same rheological properties have been studied. The creams have been sampled in two 20 ml flasks. The two flasks are introduced into two of the housings of the heating block of the device. The temperature in the flasks is stabilized at 25° C. after 10 minutes. The laser source at 650 nm is projected onto the samples. The recording pace of the speckle images follows a geometric progression with a ratio of 1.25 between a given inter-image interval and the preceding one. The experimental curves $d_2/d_{2max}$ are produced (FIG. 1a).

Figure 4A:
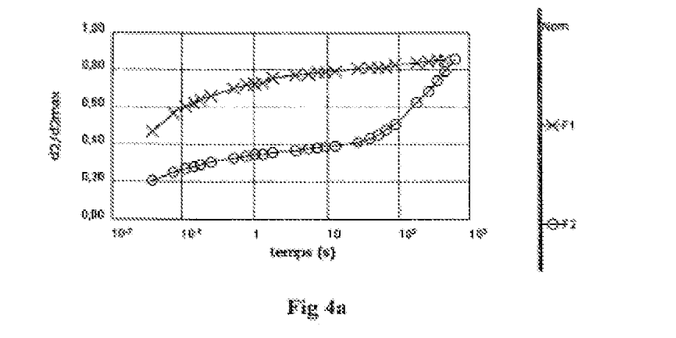
FIGS. 4a, 4b, and 4c are graphs that result from a determination.
Figure 4B:
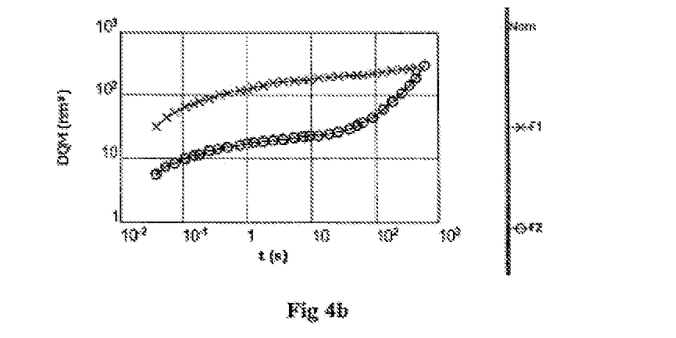

Next, the curves MSD(t) are produced for each dessert cream using the expression E (see FIG. 4b). The MSD curves give us information on the fact that the particles undergo a blocking during their scattering, which indicates the solid nature of the two products for certain frequencies.

Figure 4C:
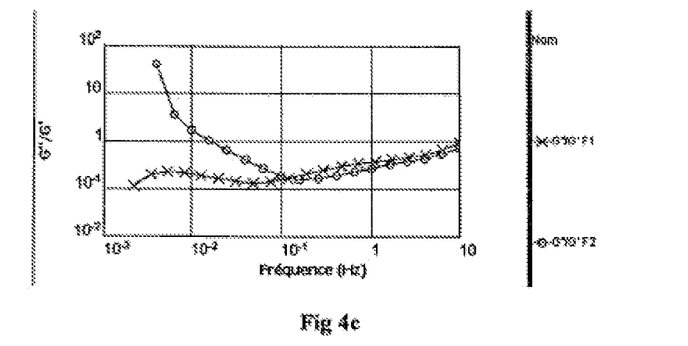

Finally, for each flask, the spectra of the viscous and elastic moduli G"(f) and G'(f) with f being the mechanical frequency are produced using the prior art teaching the conversion of MSD into these moduli (see FIG. 4c). The G"/G' ratio is calculated. It accounts for the solid nature (G"/G'<1) or liquid nature (G"/G'>1) of the product.

We note that above the frequency of 0.1 Hz, the two products have approximately the same G"/G' ratio that is less than one, and therefore they have the same solid/liquid nature for the mechanical stresses with a frequency of greater than 0.1 Hz. In contrast, the products differ at low frequency: the product F2 assumes a liquid nature. This reveals a difference in formulation that creates microstructures of different products, whereas the latter claim the same rheological properties. The liquid nature at low frequency of the product F2 can be considered as an index of less advantageous stability relative to the product F1.

The invention claimed is:

1. Method for determination of the viscoelastic properties of a complex medium starting from the movement of particles in suspension, in which a sample of the medium is placed in a device for measuring the light that is scattered by the particles in suspension, able to project a coherent light on said sample, and to detect and analyze the scattered light for calculating the inter-image distance $d_2$, characterized in that it comprises the stages that essentially consist in:
  a) Characterizing the opacity of the medium by measuring the transport length l* of said medium,
  b) Introducing a sample of said medium into a flask of given dimensions,
  c) Placing the flask in a thermostatically-controlled measuring chamber (1) of said measuring device,
  d) Projecting a coherent light beam on the sample and detecting the light that is scattered by the particles in the form of a series of sequenced images,
  e) Analyzing the movement of the particles based on time by calculating the inter-image distance $d_2$ and the ratio $d_2/d_{2max}$, $d_{2max}$ denoting a maximum value towards which $d_2$ converges asymptotically,
  f) Establishing an analytical expression E putting into direct relationship, for the value of l* that is determined in stage a), the ratio $d_2/d_{2max}$ and the mean square displacement MSD for the purpose of calculating the viscous and elastic moduli of the medium.

2. Method according to claim 1, wherein in stage f), the expression E is expressed using at least one, and preferably three, variable coefficients that can be expressed based on the opacity of the medium, and said expression E is adjusted based on the value of l* that is determined in stage a), before the calculation of the viscous and elastic moduli of the medium.

3. Method according to claim 2, wherein in stage f), the variable coefficients that are used for establishing the expression E are functions of l*, selected and recorded in a database that was previously constituted according to the stages that consist in:
  i) Preparing—in flasks of given dimensions—a range of samples of a simple fluid of known viscosity with different opacities,
  ii) For each sample of the range,
    Determining the value of l*,
    Calculating the theoretical curve $MSD_T(t)$ based on time using the Stokes-Einstein Law,
    Analyzing the movement of the particles based on time for calculating the inter-image distance $d_2$ and the ratio $d_2/d_{2max}$ and for plotting the experimental curve $MSD_E(t)$ using the expression E,
    Seeking the values of said coefficients for obtaining a theoretical curve $MSD_T(t)$ that coincides with said experimental curve $MSD_E(t)$,
  iii) For each coefficient, tracing the calibration curve representing the evolution of its value based on l*, and iv) Recording each of said curves in a database that can be called up in stage f).

4. Method according to claim 3, wherein said variable coefficients A, B, and C are selected in such a way that the calibration functions A(l*), B(l*), and C(l*) are able to be represented by straight lines.

5. Method according to claim 1, wherein in stage f), the analytical expression adopts the following form:

$$(d_2/d_{2max})^2 = 1 - \exp\{-4(A\,DQM\,k_o^2/6)^{[B+C\,\log_{10}(A\,DQM\,k_o^2/6)]}\}$$

in which A, B, and C are three variable coefficients, and $k_o$ is the wave number of the projected light.

6. Method according to claim 1, wherein in stage d), the detection of said series of images is carried out according to an increasing pace, in one or more bursts.

7. Method according to claim 6, wherein in stage d), the detection of said series of images is carried out in a single burst at an increasing pace according to a geometric progression over at least two decades.

8. Method according to claim 1, wherein in stage d), the light is projected and detected using an optical module (5) that is placed on the exterior of the measuring chamber (1), with the former having a wall penetrated by windows (3).

9. Method according to claim 1, wherein in stage c), a number of sample flasks are placed in several contiguous housings (4) located in the measuring chamber (1).

10. Method according to claim 9, wherein the optical module (5) is placed successively facing each of said flasks, and stages d) to f) are repeated for calculating the viscous and elastic moduli of each of the sampled media.

11. Method according to claim 1, wherein stage d) is carried out under conditions of stability and thermal uniformity of the samples and the measuring chamber (1) in the absence of air convection movements between the optical module (5) and the sample, and vibrations obtained from the surrounding environment.

12. Device for determining viscoelastic properties of a complex medium starting from the movement of particles in suspension, comprising means for projecting a coherent light on said medium and means for detecting and analyzing the scattered light for calculating the inter-image distance $d_2$, wherein it comprises:

An optical module (5) that comprises, on the one hand, a coherent light source (6) that is able to project a beam to a sample of the medium that is to be analyzed, and, on the other hand, means (7) for detection of the scattered light by said medium, in the form of successive matrix images, whereby said means are combined with a unit for image analysis that is able to provide values of the inter-image distance of the sample, A thermostatically-controlled measuring chamber (1) that is equipped with at least one housing (4) that is able to accommodate a flask of given dimensions that contains a sample of said medium, at a suitable distance from said optical module, Means for recording and processing data, comprising means for acquisition of values of l* that characterize the opacity of the media to be analyzed, means for analysis and calculation that are able to put into direct relationship, for a value of l*, the ratio $d_2/d_{2max}$, $d_{2max}$ denoting a maximum value towards which $d_2$ converges asymptotically, and the mean square displacement MSD, for the purpose of calculating the viscous and elastic moduli of the medium.

13. Device according to claim 12, wherein said at least one housing (4) that accommodates a flask is located in a thermostatically-controlled heating block (8), itself placed in the interior of the measuring chamber (1), at a suitable distance from the optical module (5).

14. Device according to claim 13, wherein the optical module (5) is placed on the exterior of the measuring chamber (1), the latter having an insulating wall (2) that is penetrated by windows (3) for the passage of projected and scattered light.

15. Device according to claim 12, wherein the optical module (5) is placed on the exterior of the measuring chamber (1), the latter having an insulating wall (2) that is penetrated by windows (3) for the passage of projected and scattered light.

16. Device according to claim 12, wherein the coherent light source (6) that is projected on the sample is a laser source, and the means (7) for detection of the scattered light comprise a video-camera-type matrix sensor.

17. Device according to claim 12, wherein it comprises means for neutralizing vibrations from the surrounding environment, comprising feet (9) made of damping material and a non-vibrating support structure, selected from among: a honeycomb table, an air cushion table, a weighted straw mattress.

* * * * *

UNITED STATES PATENT AND TRADEMARK OFFICE
CERTIFICATE OF CORRECTION

PATENT NO.        : 8,520,206 B2                                    Page 1 of 1
APPLICATION NO.   : 13/320598
DATED             : August 27, 2013
INVENTOR(S)       : Laurent Brunel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Fifteenth Day of September, 2015

Michelle K. Lee
*Director of the United States Patent and Trademark Office*